United States Patent
Van de Velde et al.

(10) Patent No.: US 7,411,663 B2
(45) Date of Patent: Aug. 12, 2008

(54) APPARATUS FOR GENERATING DATA FOR DETERMINING A PROPERTY OF A GEMSTONE

(75) Inventors: Marc Frans Alida Van de Velde, Antwerp (BE); Christiaan Louis Cecile Keersmaekers, Antwerp (BE)

(73) Assignee: Overseas Diamonds Technologies, Antwerp (BE)

( * ) Notice: Subject to any disclaimer, the term of this patent is extended or adjusted under 35 U.S.C. 154(b) by 0 days.

(21) Appl. No.: 11/515,399

(22) Filed: Sep. 1, 2006

(65) Prior Publication Data
US 2007/0132983 A1 Jun. 14, 2007

(30) Foreign Application Priority Data
Dec. 9, 2005 (EP) ................. 05257579

(51) Int. Cl.
*G01N 21/00* (2006.01)
(52) U.S. Cl. ......................................... 356/30
(58) Field of Classification Search ............... 356/30, 356/31
See application file for complete search history.

(56) References Cited

U.S. PATENT DOCUMENTS 6,813,007 B2 * 11/2004 Lapa et al. ................ 356/30
7,239,739 B2 * 7/2007 Lapa et al. ................ 382/141

FOREIGN PATENT DOCUMENTS

| EP | 1 319 942 A | 6/2003 |
| EP | 1795888 A1 * | 6/2007 |
| WO | WO 96/23207 | 8/1996 |
| WO | WO 99/61890 | 12/1999 |

* cited by examiner

*Primary Examiner*—Roy M. Punnoose
(74) *Attorney, Agent, or Firm*—Feldman Law Group, P.C.; Stephen E. Feldman; Paul Lim

(57) ABSTRACT

An apparatus configured to generate image data for use in determining a property of a gemstone is disclosed. The apparatus includes a support structure configured to support the gemstone at an observation position such that an axis of symmetry of the gemstone is substantially parallel to an axis of rotation of the apparatus, a light source, including a reflector having a concave surface arranged to reflect a spatially varied light pattern generally towards the observation position, the concave surface including at least one relatively reflective region and at least one relatively unreflective region and is configured to generate the light pattern, where the length of a boundary between the relatively reflective region and the relatively unreflective region is greater than the radial distance between the center and an edge of the concave surface, and a rotator configured to rotate the gemstone relative to the light pattern substantially about the axis of rotation.

20 Claims, 14 Drawing Sheets

APPARATUS FOR GENERATING DATA FOR DETERMINING A PROPERTY OF A GEMSTONE

BACKGROUND OF THE INVENTION

1. Field of the Invention

The present invention relates to electronic apparatus for generating data for determining properties of gemstones, such as cut diamonds. In particular, but not exclusively, it relates to electronic apparatus for generating data for determining properties of gemstones in which a plurality of images of the gemstone are captured for analysis under different lighting conditions.

2. Description of the Related Technology

The beauty of a gemstone, such as a cut diamond, derives from its light handling ability. What attracts the eye is the "game of light" played by a well-cut diamond as incident light is reflected and refracted off its many facets. Diamonds and other gemstones may be cut according to many different standardised cut patterns such as the standard round brilliant cut, oval, pear, marquise, radiant, princess, heart, emerald cut etc. The most popular cut is the standard round brilliant (SRB) cut as shown in FIG. 1. Diamond cutting and polishing is a highly skilled art and a well-cut diamond, having superior optical performance, will command a significant price premium over a poorly cut diamond having inferior optical performance.

When showing a cut diamond to an untrained observer, one frequently refers to the four C's of a gemstone, being its carat weight, its clarity, its cut and its color. Carat weight, clarity and color can be relatively easily measured objectively and are therefore generally useful. Cut may also be specified or measured in terms of the geometry of the various facets. However, what really matters is the light handling ability of the gemstone and reference is often made to more subjective parameters of a cut diamond, such as its brilliance (the intensity of light returned), scintillation (fast and local fluctuations in the light returned as the diamond moves relative to the lighting conditions), fire (the dispersion of white light into spectral colors) and symmetry (the symmetry of light patterns such as the so-called "hearts and arrows"). It can be difficult, particularly for an untrained observer, to make a personal appraisal of these subjective parameters. It can also be difficult to compare the light handling abilities of two diamonds with the same carat weight, clarity and color, and therefore to appreciate why one is more valuable than the other.

It is recognized that properties such as brilliance, fire and symmetry should be derived, whether by experimental observation or theoretical computer modelling, under a variety of lighting conditions. Moreover, with the property of scintillation it is clearly essential to observe or model the diamond under a variety of lighting conditions. Electronic apparatus for capturing images of gemstones under varying lighting conditions for analysis are known.

The present applicant previously filed a European patent application EP 1319942 for an apparatus designed to measure properties of a gemstone. In this application, it is described that properties of a gemstone are determined by capturing images of a gemstone at a number of rotational positions relative to a spatially varied light pattern. The spatially varied light pattern is produced by a reflector with two regions, one relatively reflective, and the other relatively non-reflective. The boundary between the two regions lies in a plane parallel to the axis along which observation of the gemstone takes place. That is, the length of the boundary between the two regions is at a minimum length, and is formed by a straight line from the centre of the reflector, through which the gemstone is observed, to its closest edge.

International Patent Publication number WO 96/23207 describes a device which captures color images of a gemstone placed in an analysis chamber and illuminated by a uniform annular light which may be moved along an axis such that the gemstone may be illuminated from a plurality of different angles. The device performs a spectral analysis of the captured images using a tuneable optical band pass filter to determine the color of the gemstone. Digital images of the gemstone may also be stored, displayed or transmitted over a data network.

The website (www.gemex.com) of GemEx Systems, Inc, a U.S. company, describes a device called the BrillianceScope Analyser which is described as an imaging spectrophotometer. Color images of a diamond are captured in a controlled lighting environment consisting of six lighting angles, five of which provide reflected light and one of which provides diffuse lighting. These images may then be analysed to generate a report on the diamond. The BrillianceScope Analyser device operates on the same principle as the device described in International Patent Publication number WO 96/23207 referred to above, in that the gemstone is placed in an analysis chamber and illuminated by a uniform annular light which may be moved along an axis such that the gemstone is illuminated from different angles. The images may be analysed by a computer, and the properties of "white light", "colored light" and "scintillation" for a diamond are determined and displayed on three line chart scales from 'low', to 'medium' to 'high'. Captured images may also be shown in a repeating sequence in one display area, giving the effect of light movement. Images of two gemstones may be displayed side-by-side for comparison.

International Patent Publication number WO 99/61890 describes a system for the standardised grading of gemstones. A gemstone is subject to a plurality of incident light sources and images are captured for analysis. Images of the gemstone, such as a SRB cut diamond, may be captured from various viewpoints such as from the pavilion, from the crown and side-on. The gemstone is supported by a rotatable platform which is rotated when images are being captured from a side-on viewpoint to obtain profile and color images from a variety of rotational positions and to detect internal flaws and inclusions. When capturing images from above and below the gemstone, the platform is moved along an axis from a level position to a down and an up position respectively. The fixed focal length camera is also moved along an axis to focus on the gemstone when the platform is moved between the up, down and level positions. A captured image may be analysed by a processor to obtain color measurements and measures of the brilliance and scintillation of the gemstone.

U.S. Pat. No. 4,900,147 describes a method and apparatus for mapping the crystalline structure of a diamond using Roman spectroscopy.

U.S. Pat. No. 2,332,755 describes a branding viewer for displaying a brand mark or a portion of a surface of a diamond.

SUMMARY OF CERTAIN INVENTIVE ASPECTS

One embodiment is an apparatus configured to generate image data for use in determining a visual property of a gemstone. The apparatus includes a support structure configured to support the gemstone placed at an observation position, the support structure being configured to support the gemstone having an axis of symmetry such that the axis of symmetry is parallel to an X axis passing through the observation position, a light source configured to illuminate the gemstone with a spatially varied light pattern, a rotator, configured to rotate the gemstone relative to the light pattern substantially about the X axis, a camera arranged to capture electronic images of light of the gemstone and to output the images as image data, and a controller configured to control the rotator and the camera such that the camera is configured to capture an electronic image of the gemstone at each of a plurality of rotational positions of the support structure relative to the light pattern, the images being captured generally along the X axis, the light source including a reflector having a concave surface arranged to reflect light generally towards the gemstone. The concave surface has at least one relatively reflective region and at least one relatively unreflective region, whereby the light pattern is generated, where the length of a boundary between the relatively reflective and relatively unreflective regions is greater than the radial distance between the center and the edge of the concave surface.

Another embodiment is a apparatus configured to generate image data for use in determining a property of a gemstone The apparatus includes a support structure configured to support the gemstone at an observation position such that an axis of symmetry of the gemstone is substantially parallel to an axis of rotation of the apparatus, a light source, including a reflector having a concave surface arranged to reflect a spatially varied light pattern generally towards the observation position, the concave surface including at least one relatively reflective region and at least one relatively unreflective region and is configured to generate the light pattern, where the length of a boundary between the relatively reflective region and the relatively unreflective region is greater than the radial distance between the center and an edge of the concave surface, and a rotator configured to rotate the gemstone relative to the light pattern substantially about the axis of rotation.

DETAILED DESCRIPTION OF CERTAIN INVENTIVE EMBODIMENTS

Figure 1A:
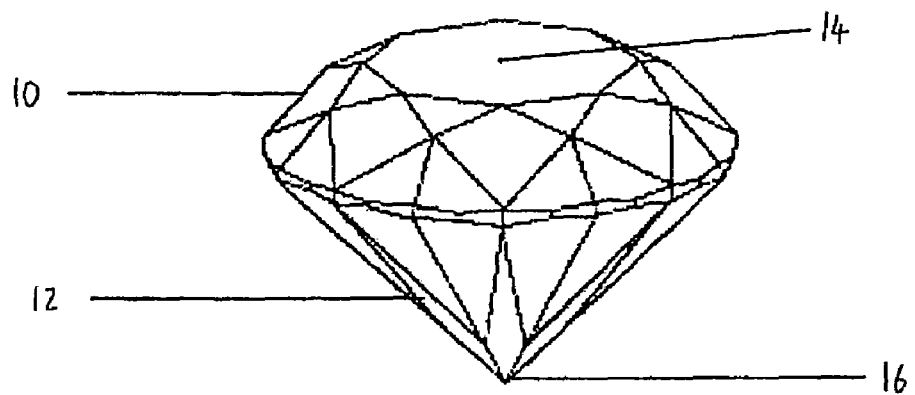
FIGS. 1a and 1b show a standard round brilliant cut diamond from an elevated side-on perspective and from a top-down view, respectively.
Figure 1B:
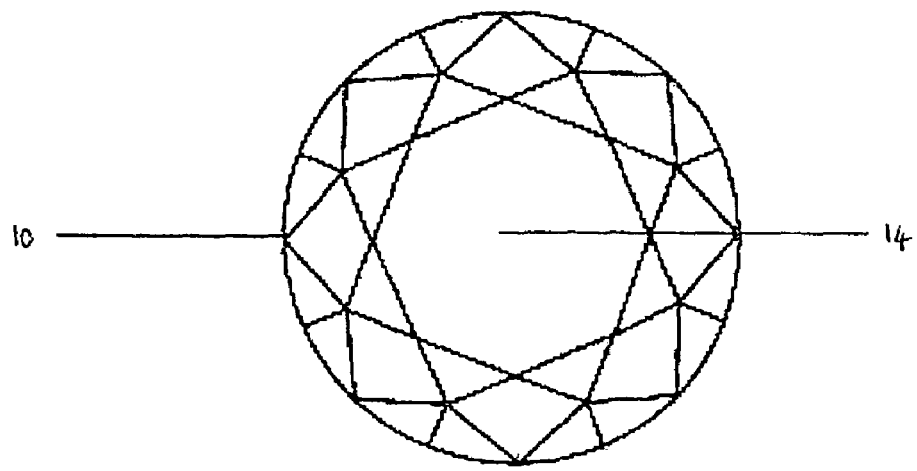

FIGS. 1a and 1b show the geometry of a standard round brilliant (SRB) diamond. FIG. 1a shows the diamond from an elevated side-on view. The top most domed-shaped portion of the diamond is known as the crown 10. The bottom most conical portion of the diamond is known as the pavilion 12. At the top of crown 10 at the centre is a relatively large facet known as the table 14. The bottom most point of the pavilion 12 is known as the culet 16. FIG. 1b shows the SRB diamond from a top-down view, looking along an axis from the centre of the table 14 through the culet 16. There are 32 facets on the crown 10 of the SRB cut diamond, not including table 14, and 24 facets on the pavilion 12, not including culet 16. It can be seen that the radial facets of the SRB cut diamond (56 in total plus one for the table and one for the culet) have an 8-fold symmetry about an axis passing though the centre of table 14 and culet 16.

Figure 2:
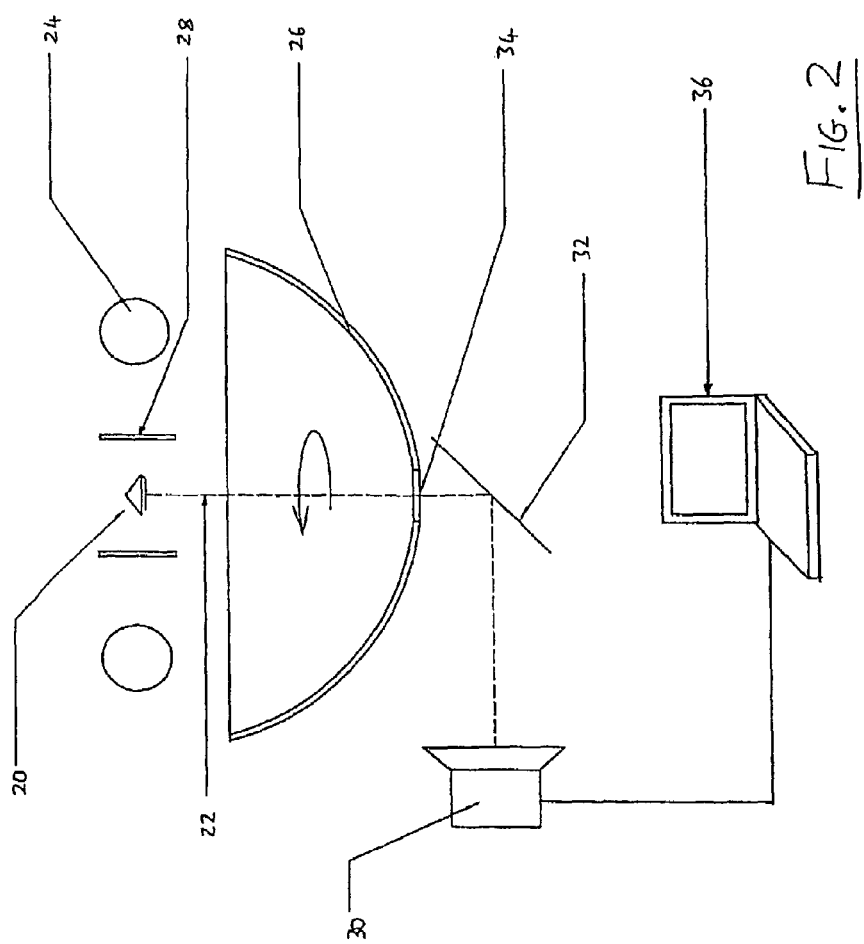
FIG. 2 shows an apparatus for generating data for determining a property of a gemstone according to the present invention.

FIG. 2 shows a cross-sectional view of an apparatus for generating data for determining properties of a gemstone according to one embodiment. A gemstone such as a cut diamond 20 is placed on a platform (not shown) at an observation position with its table-side face-down. The platform is an optically clear glass plane of regular thickness arranged within the apparatus so that it is substantially horizontal when the apparatus is in a horizontal position. The platform may be coated with an anti-reflection coating and provided with a small ring underneath to reduce glare. The apparatus is mounted in a housing (not shown) which prevents external light from reaching the diamond 20 and dust from entering the mechanical and optical components. The housing has a access lid above the platform for placing and removing a gemstone to be measured. The inner surface of the housing and lid above the region of the platform is coated with an unreflective material so that substantially no light is reflected back from the lid or housing towards the gemstone or platform.

Diamond 20 is illuminated by a light source, such as an annular light 24, which may, for example, comprise a fluorescent tube light or halogen light. Annular light 24 emits visible light of frequency comparable to daylight. A suitable annular light is a Stocker and Yale microscope illuminator with a White 5500HC fluorescent ring light having a color temperature of 5500° K, which produces a light close to Northern daylight. Light from annular light 24 is prevented from directly reaching diamond 20 by an annular baffle 28 disposed between the annular light 24 and the diamond 20. However, light from annular light 24 is reflected off a concave surface 26 of a reflector and generally towards diamond 20. The reflector may be a semi-spherical shell centred on the observation position with the inner surface of the shell being concave surface 26.

The reflector is mounted within the apparatus such that concave surface 26 is rotatable about an axis 22 perpendicular to the platform and such that when diamond 20 is placed at the observation position, the centre of its table and its culet lie approximately along axis 22. Annular light 24 and annular baffle 28 are stationary and disposed within the apparatus such that they are also perpendicular to and centred around axis 22. A stepper motor (not shown) is provided for rotating the reflector, and concave surface 26, about axis 22.

A viewing hole 34 is present at the bottom of the reflector and concave surface 26 where they meet axis 22. A digital camera having a charged couple device (CCD) sensor array, or a complementary metal-oxide semiconductor (CMOS) sensor array, and capable of being controlled by a personal computer (PC), is positioned within the apparatus such that it can capture an image of diamond 20 along the axis 22. The camera is a color camera having a fixed focal length, at least a 640×480 resolution, a memory capable of storing at least one image, and a data communication interface, compatible with standards such as the Universal Serial Bus (USB), RS 422 parallel port or IEEE 1394 "Firewire" standards, for transferring captured image data to an external device, such as a PC. The camera is focussed on the plane made by the topmost surface of the platform on which diamond 20 is placed, and has a suitable depth of field such that sharp images may be captured of gemstones of the largest size reasonably expected to be measured. An optically clear mirror 32 may be disposed within the apparatus so that the light path between camera 30 and diamond 20 need not be a straight line, thereby enabling a more compact format of apparatus. A suitable digital CCD camera is a Unibrain Fire-i Digital CCD color camera with a resolution of 640×480 or a Unibrain Fire-i400 Industrial version with a similar resolution. A suitable digital CMOS camera is a Silicon Imaging MegaCamera SI-3170 RGB camera, with a maximum resolution of 2056×1560, a 12-bit per pixel color depth.

The apparatus, including the light 24, baffle 28, reflector with concave surface 26, mirror 34, stepper motor, camera 30, and housing, but not including the PC, is compact in size (having dimensions of approximately 123 mm×112 mm×200 mm) and lightweight (approximately 3.875 kg).

Camera 30 and the stepper motor are connected to and controllable by a PC 36. PC 36 may be a portable PC such as a laptop or notebook computer having an Intel Pentium III central processing unit (CPU), 128 megabytes of memory, an LCD panel screen and a 10 gigabyte hard disc drive. PC 36 has a USB port, a parallel port and/or IEEE 1394 "Firewire" port for connecting to the camera and stepper motor, and a 2D video processing chipset for frame grabbing. By means of a suitable computer program, as will be described in greater detail below, PC 36 controls the stepper motor to rotate concave surface 26 through a series of predetermined rotational positions. PC 36 also controls camera 30 to capture images of diamond 20 at a suitable frame rate such that an image may me stored at each of the series of rotational positions of concave surface 26. The image data captured by camera 30 is transferred to PC 36 in the form of a bitmap or other suitable image file format for display and analysis. The image data is transmitted as a continual live image feed to the PC 36.

The range of angles through which concave surface 26 is rotated is dependent upon the symmetry of the light pattern reflecting off concave surface 26. With a light pattern having a 4-fold symmetry, for example, images are captured at a plurality of rotational positions as concave surface 26 is rotated through a 90° range. Within the range, the number of images captured at different rotational positions for use in analysis depends on the cut pattern of the gemstone being measured, or the cut pattern of the most faceted gemstone likely to be measured. Generally, the number of images should be at least 4 times the number of differently angled facets within the range through which concave surface 26 is rotated. Thus, with a SRB cut diamond having 32 differently angled facets in its crown and pavilion and thus 8 differently angled facets within a 90° range, at least 32 images (4*8) should be captured over the 90° range. For general purpose, it has been found that a generally suitable number of images to be captured is 45. Thus, over a 90° range, concave surface 26 is rotated in steps of 2°. It will be understood that higher or lower numbers of images may be used as appropriate to the cut pattern of the gemstone, the accuracy of measurement required and the processing capabilities of the PC 36.

Figure 3A:
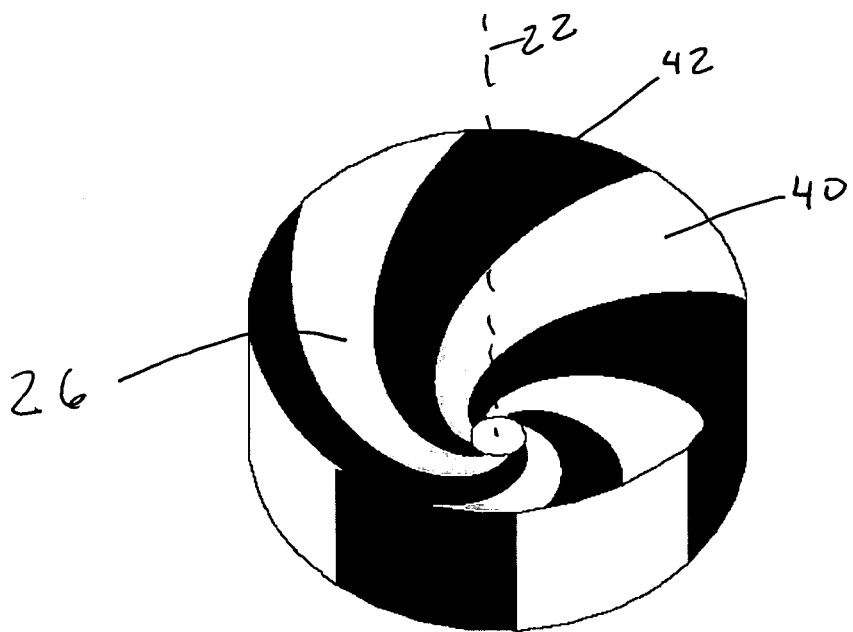
FIGS. 3a, 3b, 3c and 3d show the concave surface 26 of the apparatus of FIG. 2 having exemplary patterns of relatively reflective and relatively unreflective regions.
Figure 3B:

FIGS. 3a and 3b show the concave surface 26 looking down from the diamond observation position along axis 22. Concave surface 26 has a plurality of relatively reflective regions 40 and relatively unreflective regions 42 formed by coating the surface with relatively reflective and relatively unreflective materials.

FIG. 3a shows one configuration of regions 40 and 42 in which concave surface 26 is divided into eight equal sectors, arranged around the axis 22, which are alternately relatively reflective and relatively unreflective. The boundary between the relatively reflective and relatively unreflective sectors on the concave surface is greater than the minimum length. That is, in this embodiment, the boundary is formed as a spiral moving out from the center of the concave surface 26 at a constant angle along the boundary path. Therefore, a line from each point along the boundary, through the center of the concave surface 26 forms an angle with the boundary. The angle, in this embodiment, is in the range between about plus and minus 45°. Further examples could be used where the angle between the line and the boundary is in the range between about plus and minus 35°, or between about plus and minus 25°. Other angles may also be used. This spiral configuration produces an increased boundary length along the boundary between the relatively reflective and relatively unreflective regions on the concave surface 26.

FIG. 3b shows a different configuration for the boundary between the relatively reflective and relatively unreflective regions. In this configuration, the boundary is formed by folding the spiral (or swirl) of FIG. 3a back and forth eight times over the length of the boundary.

Figure 3C:
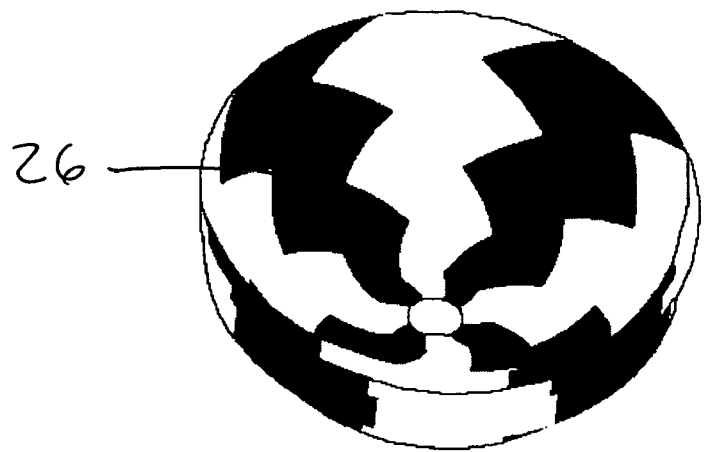

FIG. 3c shows a further configuration of the boundary between the relatively reflective and relatively unreflective regions on the concave surface 26. In this configuration, the number of discontinuities shown in FIG. 3b is reduced such that the spiral (or swirl) is folded back and forth only five times.

It will be understood that the form of the boundary between the relatively reflective and relatively unreflective regions may be modified considerably, while bearing in mind that the important aspect is that the length of the border between the relatively reflective and unreflective regions is greater than the minimum length—the radial distance from the center to the edge of concave surface 26.

Figure 3D:
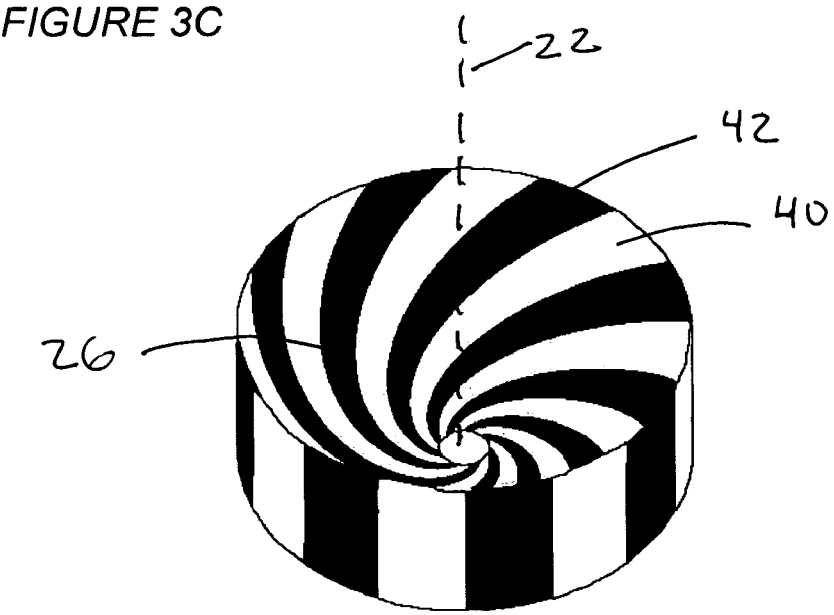

FIG. 3d shows an adapted version of FIG. 3a with a further configuration of regions 40, 42 in which concave surface 26 is divided into 16 equal sectors, arranged around the axis 22, of alternate relatively reflective and relatively unreflective regions. It can be seen that the configuration of regions 40 and 42 of FIGS. 3a to 3c each have a four-fold symmetry about the axis 22 whereas the configuration of regions 40 and 42 of FIG. 3d each have an eight-fold symmetry about axis 22. The eight-fold symmetry of FIG. 3d can also be applied to the configuration of FIGS. 3b and 3c. Also other configurations of relatively reflective regions 40 and relatively unreflective regions 42 are envisaged within the scope of the present invention. For example, the boundary between the relatively reflective and relatively unreflective regions may be formed from other patterns, such as straight zigzags, curved zigzags or a combination thereof. Concave surface 26 may have a matte finish.

During operation of the apparatus, it can be seen that the light reflecting off concave surface 26 towards the diamond 20 at its observation position has a spatially varied pattern determined by the configuration of relatively reflective regions 40 and relatively unreflective regions 42. In particular, the light pattern, as observed in the plane of the platform, will have a series of radial peaks and troughs of light intensity corresponding to the configuration. Thus, with the configuration of FIG. 3a, the light pattern will have four radial peak lines and four radial trough lines. Similarly, with the configuration of FIG. 3b, the light pattern will have 8 radial peaks and 8 radial troughs. Furthermore, with diamond 20 table-side down on the platform, the light will be reflected generally towards the crown at a broad range of angles of incidence relative to axis 22, as predominantly occurs when diamonds are mounted in rings and other jewelry for everyday use.

The selection of a particular configuration of relatively reflective regions 40 and relatively unreflective regions 42 is dependent upon the standardised cut of diamond 20. For example, a diamond of SRB cut has an eight-fold symmetry as described above, and a suitable configuration of regions 40 and 42 would be that as shown in FIG. 3a, in which there are eight sectors in total—four relatively reflective sectors 40 and four relatively unreflective sectors 42. Thus, the light pattern reflecting of concave surface 26, having four radial peaks and four radial troughs corresponds to the symmetry of the cut gemstone in that adjacent symmetrical sectors of the gemstone (of 45°) will receive corresponding radial light pattern sectors (of 45°) having adjacent peaks and troughs. As concave surface 26 is rotated through 90°, the intensity of light as observed at any radial line in the plane of the platform and about axis X, will go through a single complete cycle having a single peak and a single trough.

PC 36 may run a standard operating system, such as Microsoft Windows XP or the like. PC 36 also executes a computer program arranged to control the stepper motor to rotate concave surface 26 and to control camera 30 to capture and transfer to PC 36 images of diamond 20 at each of the predetermined rotational positions, for example, 45 images taken at rotational steps of 2° over a total range of 90°. Control over the stepper motor is achieved by using a conventional stepper motor control circuit, such as a Motorola MC 3479 stepper motor controller, to interface between PC 36 and the stepper motor and executing corresponding program elements on PC 36 for sending digital control signals to the stepper motor control circuit. Control over camera 30 is achieved using the camera's inbuilt control interface and executing corresponding program elements on PC 36 for sending digital control signals to camera 30.

Figure 4:
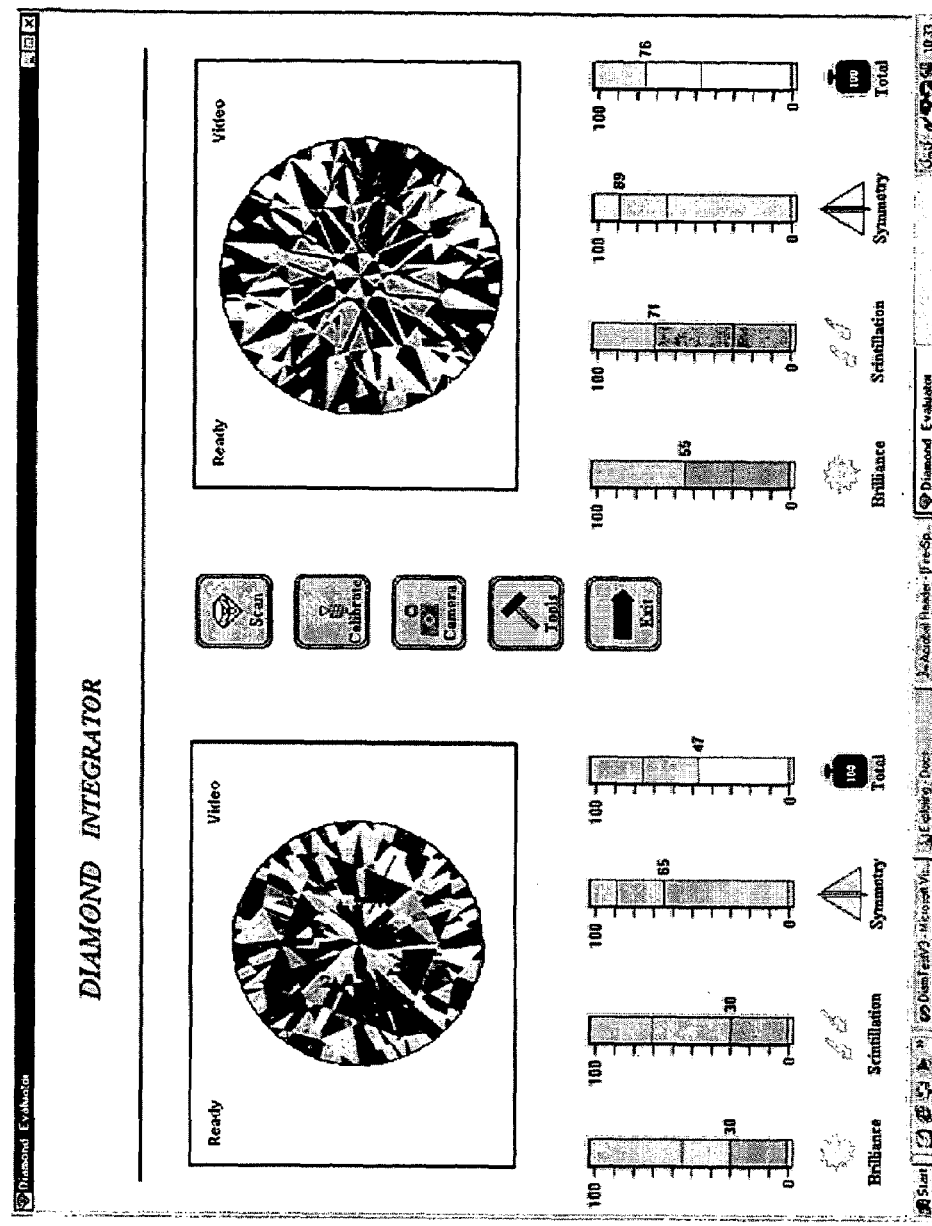
FIG. 4 shows a screen shot of the main screen of a computer program for analysing images of gemstones according to the present invention.

The program elements controlling the stepper motor and camera 30 are themselves under control of a main computer program executing on PC 36 and able to receive user instructions via a user interface to cause the series of images of diamond 20 to be captured and transferred from camera 30 to the PC 36, to analyse the images using various algorithms to obtain measurements of optical properties of diamond 20 and to display the images on the screen of the PC 36. FIG. 4 shows a screen shot of the main menu screen of the computer program. On the right and left sides of the main menu screen are images of two different diamonds, captured in separate scanning operations. An image of a diamond on the right or left sides of the main menu screen may be a "live" image as currently being captured by camera 30 or a "video" image as previously captured during a scanning operation and stored in the hard disk drive of the PC 36. A "video" image may be presented as a moving image with the diamond being shown in consecutive rotational positions. Beneath each image are measurements of the diamond's optical properties of brilliance, scintillation and symmetry represented in numerical format (0 to 100) and as a graphical bar chart. Algorithms for calculating these measurements will be described below. An average of the three measurements is also provided labelled "Total" giving an overall measure of the three optical properties. Thus, a user, such as prospective buyer can compare two diamonds, scanned in two separate scanning operations, side by side both visually on PC 36 screen and in terms of objective measurements of the optical properties of brilliance, scintillation and symmetry.

Five push buttons are presented in the centre of the screen for user control of the computer program and apparatus. A "Scan" push button is provided for causing the computer program to initialize a scan of diamond 20. Initially, diamond 20 is manually placed table-side down on the platform and centred on axis 22. This may be assisted by observing the live image of the diamond displayed on PC 36 screen. Then, a rotator, such as a stepper motor is controlled to rotate concave surface 26 to a "home" position and then to each of the series of rotational positions, for example 45 positions over a 90° range in steps of 2°. Frames grabbed from camera 30 at each of these positions are stored in the hard disc drive of PC 36 for later display and analysis. The results of analysis, ie the measurements of brilliance, scintillation and symmetry, are then displayed.

A "Calibrate" push button is provided for calibrating the system to compensate for variations in the intensity of the light produced by annular light 24. Calibration is performed by rotating concave surface 26 to a predetermined position, and placing an angled mirror on the platform in a predetermined position, such that camera 30 views a known portion of concave surface 26. The known portion concave surface 26 may comprise relatively reflective and relatively unreflective regions 40, 42. An image captured by camera 30 of the known portion of concave surface 26 is then analysed by integrating the light intensity levels over all pixels to determine a total light intensity level received. The total light intensity level is then used to adjusts gain and brightness settings of camera 30. Calibration is preferably performed at regular intervals and immediately prior to scanning.

A "Camera" push button is provided for altering the default settings of the camera. A "Tools" push button is provided for selecting various options for the computer program such as a) whether the computer program determines the circumference of a gemstone automatically or manually; b) if manually, for providing user interface means to indicate it; c) how fast concave surface 26 is rotated; and d) the frequency with which stored frames, captured at different rotational positions, are sequentially displayed on the screen of PC 36. An "Exit" push button is also provided for closing exiting the computer program.

To calculate the three measures of brilliance, scintillation and symmetry, from the stored images, three separate algorithms are used. In each case, the main computer program first analyses the images to determine the circumference of diamond 20 and its centre point. The circumference is determined by first summing the light intensity levels at each pixel over all the images at different rotational positions, for example 45 images, to obtain a composite image. Then, all pixels of the composite image having a light intensity level above a predetermined threshold (representing a light level slightly above the level of the black background) are selected. Then the smallest circle containing all the selected pixels is determined and this is defined as the circumference of diamond 20.

Figure 5:
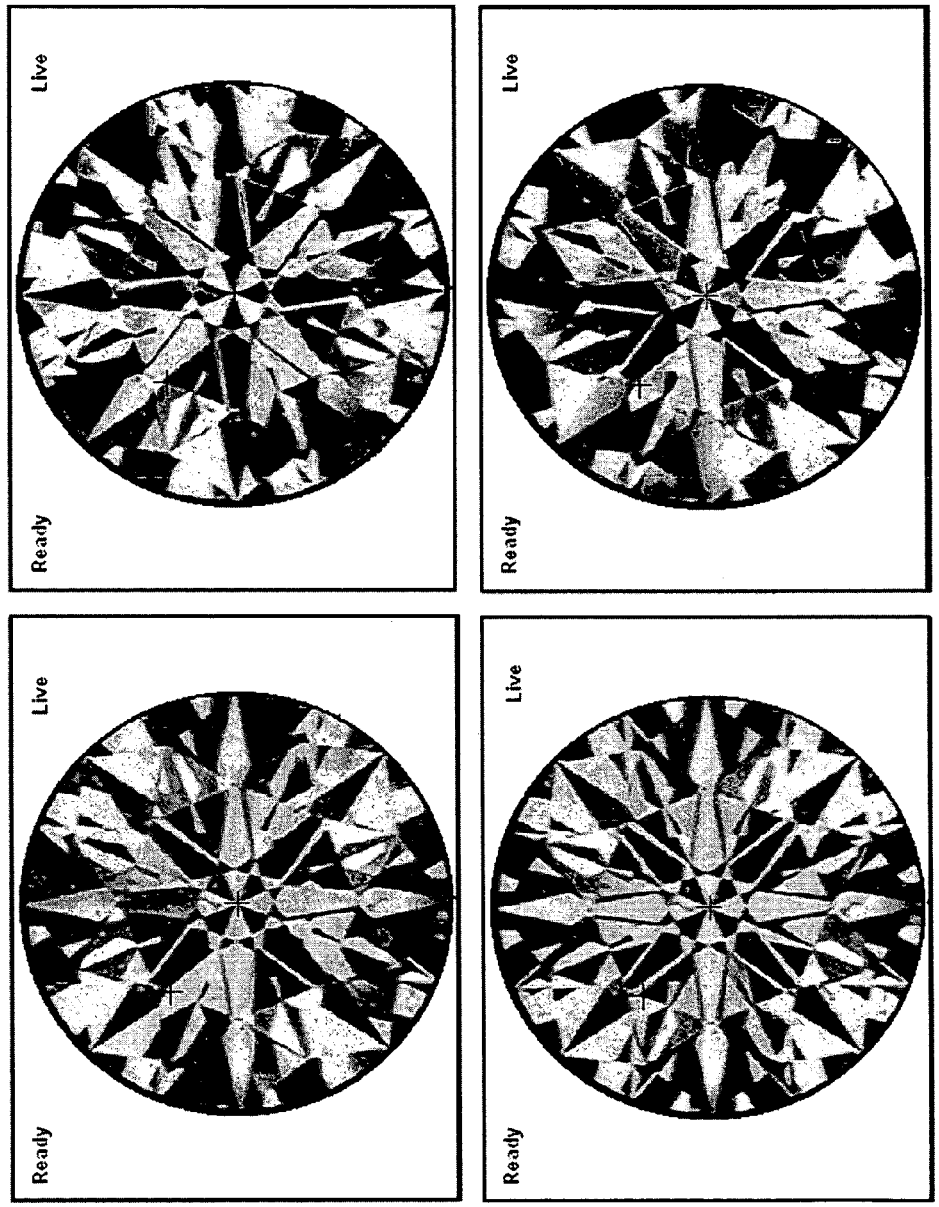
FIG. 5 shows four images of a cut diamond captured at different rotational positions.

Once the circumference and centre of diamond 20 is determined, the three algorithms are executed to calculate measurements of the three optical properties only in respect of pixels contained within the circumference and excluding pixels outside the circumference. FIG. 5 shows four images of a cut diamond captured at different rotational positions together with a circle defining the circumference of the diamond and a cross marking the centre point. It can be seen that various geometrical patterns of light and dark regions are formed and, in different rotational positions, the regions appear either relatively light or relatively dark.

To calculate a measure of the brilliance of diamond 20, the average light intensity level (ie brightness) is determined over each pixel within the circumference of diamond 20 and for each of the stored images at different rotational positions. Thus, if there are n pixels in the circumference of diamond 20, and 45 images at different rotational positions, the light intensity level is averaged over 45*n pixels in total. This results in an average light intensity level for diamond 20 over all images at different rotational positions, which provides an objective measure of the brilliance of diamond 20.

To calculate a measure of the scintillation of diamond 20, the difference in light intensity levels (ie brightness) between a pixel from a first image (captured at a first rotational position) and its corresponding pixel (at the same coordinate position) from a second image (captured at a second rotational position, one rotational step after the first rotational position) is determined. This is repeated for all pixels within the circumference of diamond 20 in the first and second images, and for all pairs of first and second images captured at rotational positions which are one rotational step apart. Thus, if there are n pixels in the circumference of diamond 20, and 45 images at different rotational positions, 44*n differences are calculated. The number of times the absolute difference in light intensity levels is greater than a predetermined threshold is counted for all pixels in the circumference and for all pairs of images which are one rotational step apart. The ratio of this number over the total number of pixel pairs, 44*n, gives an objective measure of the scintillation of diamond 20.

To calculate a measure of the symmetry of diamond 20, for the composite image, composed of the stored images at each of the different rotational positions, pixels within the circumference of diamond 20 are divided into 8 approximately equal radial sectors about the centre of diamond 20. The number of sectors is chosen to correspond to the 8-fold symmetry of the SRB cut pattern. Thus, if there are n pixels within the circumference of diamond 20 in an image, each sector has approximately n/8 pixels. Then, the difference in light intensity levels (ie brightness) between each pixel in each of the 8 sectors of an image and its corresponding pixels (ie the corresponding pixels as rotated by i×45°, where i=1 to 7) in the seven other sectors of the same image is determined. Thus (7+6+5+4+3+2+1)*n/8=7*n differences are calculated. The average of the absolute values of these differences is then calculated to give an objective measure of the symmetry of diamond 20.

In this embodiment, a measure of the fire of a diamond 20 may be calculated by using an algorithm similar to that for determining scintillation. However, instead of measuring the difference in light intensity levels, the difference in the relative proportions of color components (i.e. red, green, and blue (RGB)) between a pixel from a first image (captured at a first rotational position) and its corresponding pixel (at the same coordinate position) from a second image (captured at a second rotational position, one rotational step after the first rotational position) are determined. This is repeated for all pixels within the circumference of diamond 20 in the first and second images, and for all pairs of first and second images captured at rotational positions which are one rotational step apart. For each pixel pair, the number of times the absolute difference in the relative proportions of any of the three color components is greater than a predetermined threshold is counted for all pixels in the circumference and for all pairs of images which are one rotational step apart. The ratio of this number over the total number of pixel pairs gives an objective measure of the fire of diamond 20.

With the concave surface 26 being formed as discussed above, an improved fire reading is obtained when using the above method. The reason for the improved fire measurement results from the configuration of the boundary between the relatively reflective and relatively unreflective regions on the concave surface 26. That is, the individual color elements within the color streaks reflected off the facets of the diamond are gradually moved from one region to another region when there is a relative rotation between the concave surface 26 and the diamond. In earlier designs of the concave surface, the boundary between the relatively reflective and relatively unreflectively regions was formed using the minimum length possible along the plane of the viewing axis. However, the angle at which the color elements in the light reflected off the facets of a diamond are located on the concave surface 26 results in many of the color streaks (red, green and blue) being moved from one region to another region during one rotational movement. That is, the previous design has the disadvantage that all the individual colors within the majority of color streaks jump from one region to the other region in one rotational movement, therefore only providing a white or black response and so not providing an accurate fire measurement.

FIGS. 6a to 6d show color streaks of various cuts of diamond to indicate the angles at which the color streaks are reflected onto the concave surface of a reflector according to various embodiments.

Figure 6A:
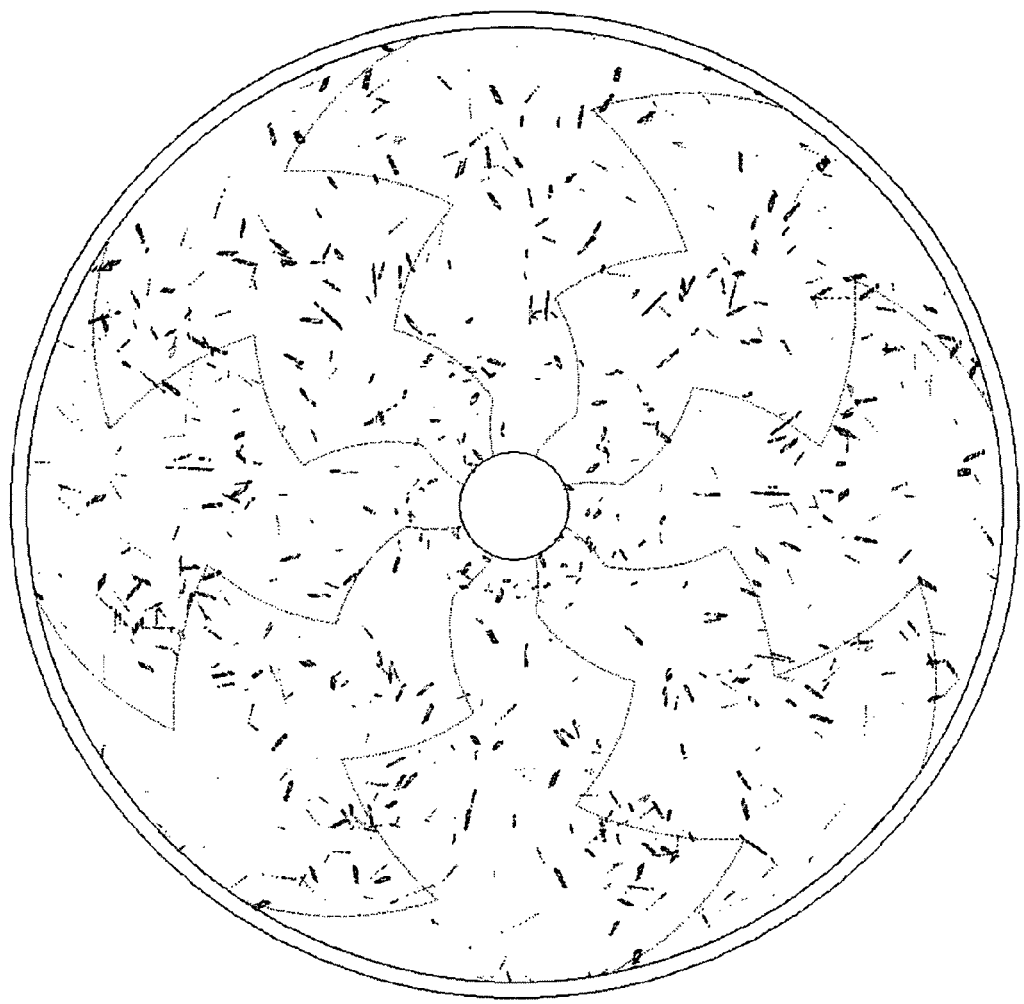
FIGS. 6a to 6d show the color components of light reflected off facets of different diamond cuts.
Figure 7A:
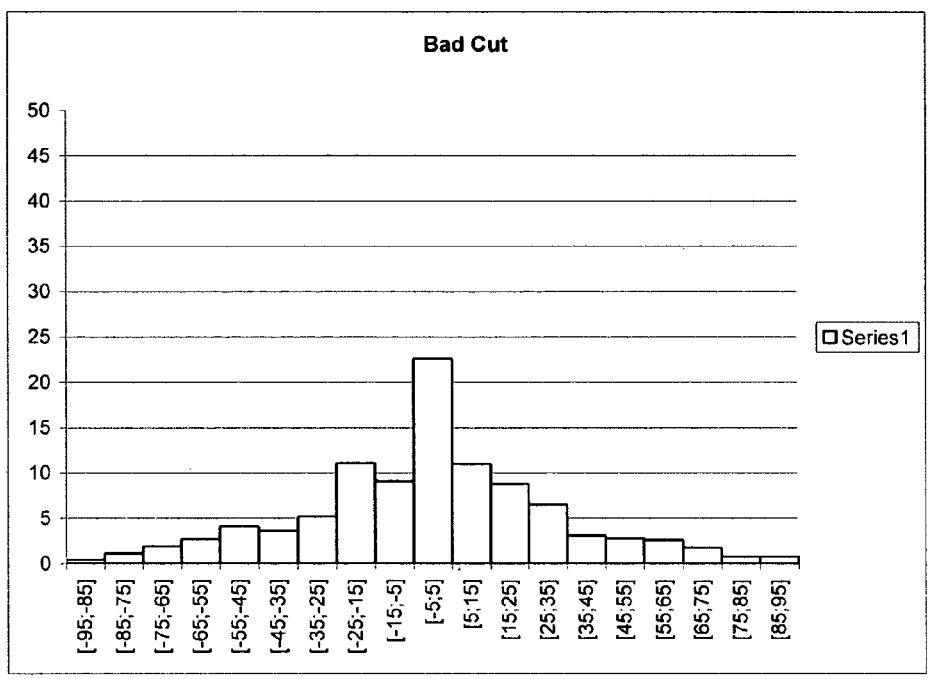
FIGS. 7a to 7d show the distribution of the angles at which the color components are reflected off facets of different diamond cuts.

FIG. 6a shows the color streaks resulting from a diamond considered to be a "bad stone". FIG. 7a shows the distribution of the angles at which the color streaks are located on the reflector surface, relative to the plane of the observation position. It can be seen that a large proportion of the color streaks are positioned within a ranges of angles between plus and minus 5° from the observation plane at any particular rotation point. Further, it can be seen that the greater number of color streaks are positioned within a range of angles between plus and minus 25° from the plane of the observation position. Further, it is shown that the majority of color streaks are positioned between angles of plus and minus 35° from the plane of the observation position.

Figure 6B:
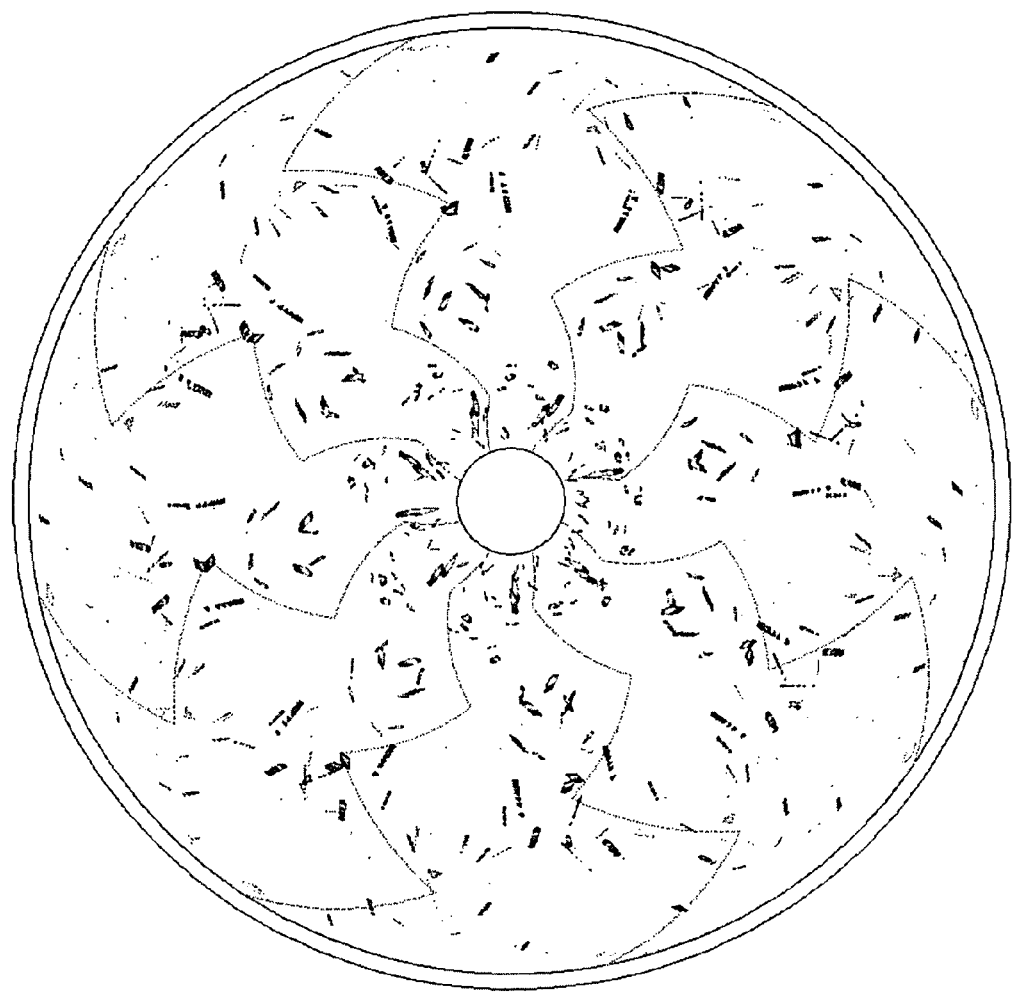
Figure 7B:
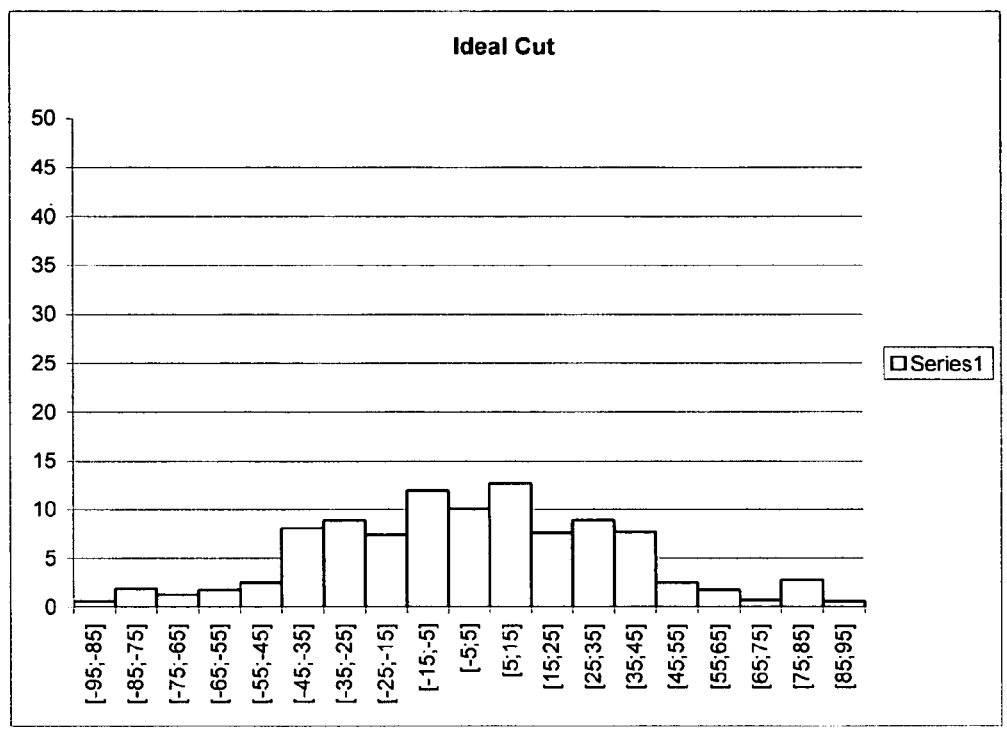

Referring to FIGS. 6b and 7b, it can be seen that, for an "ideal cut" diamond, the majority of color streaks are positioned within a range of angles between plus and minus 45° from the plane of the observation position.

Figure 6C:
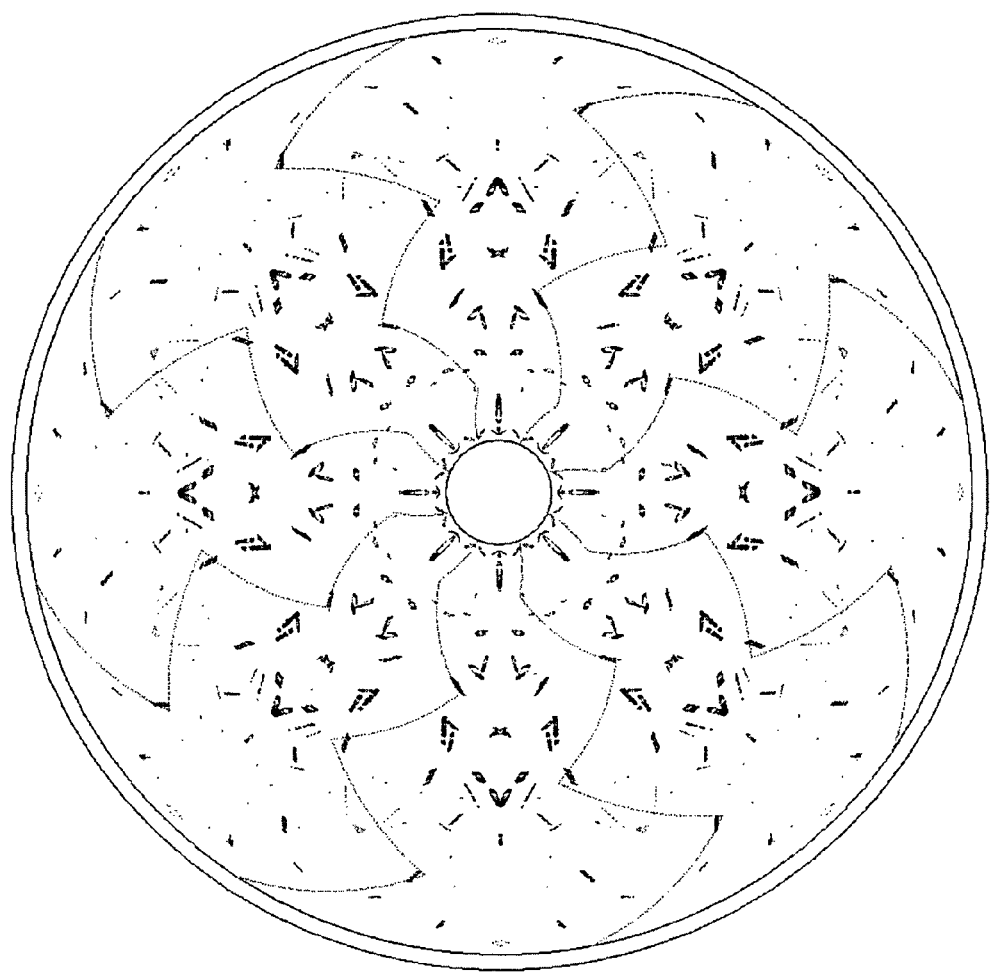
Figure 7C:
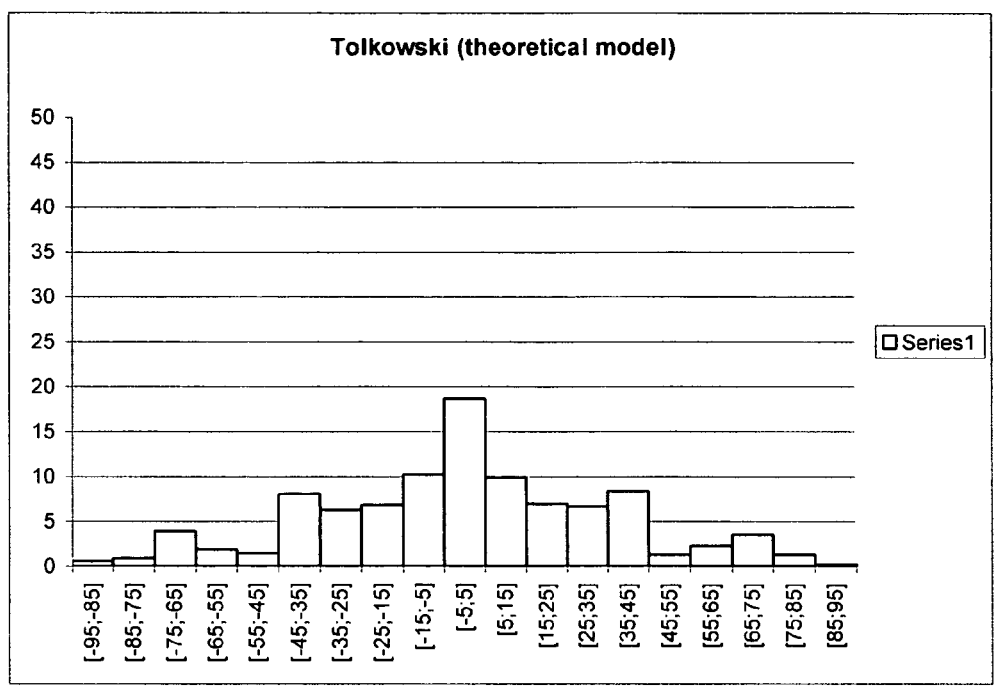

Referring to FIGS. 6c and 7c, it can be seen that, for a "Tolkowski" cut diamond, the majority of color streaks are positioned within a range of angles between plus and minus 45° from the plane of the observation position.

Figure 6D:
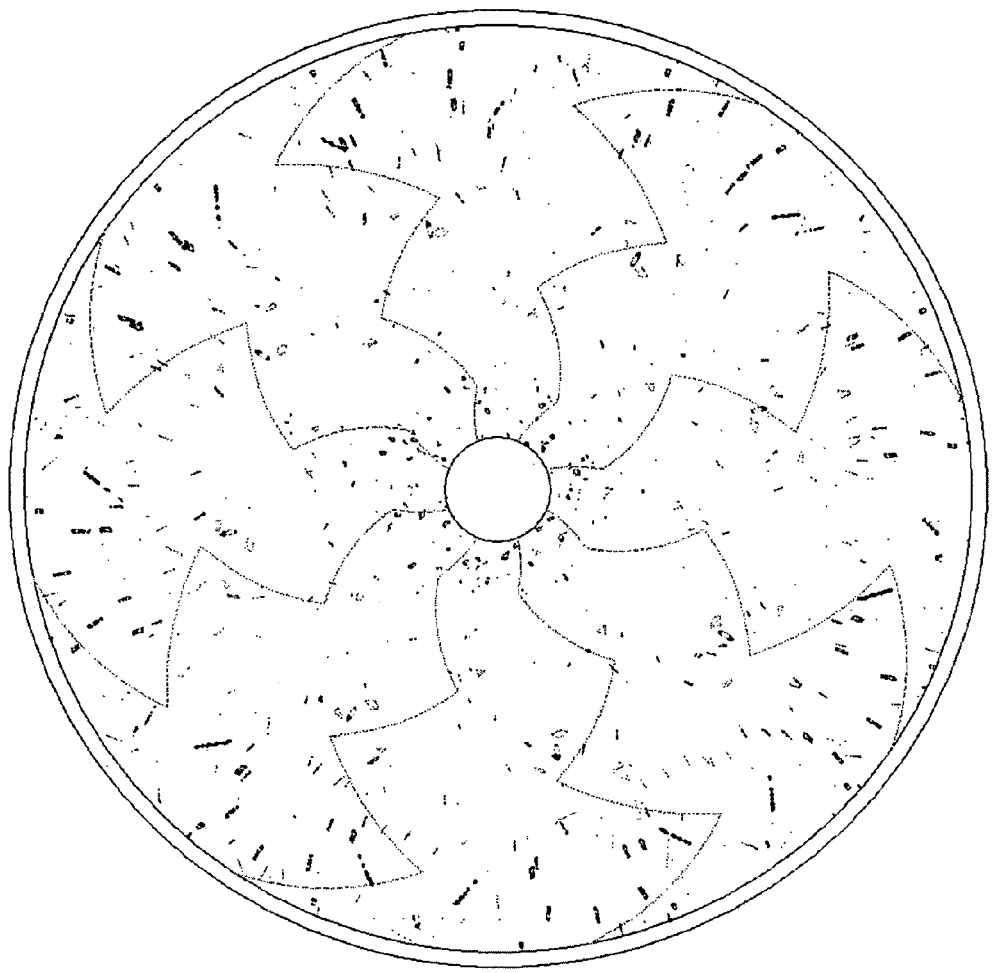
Figure 7D:
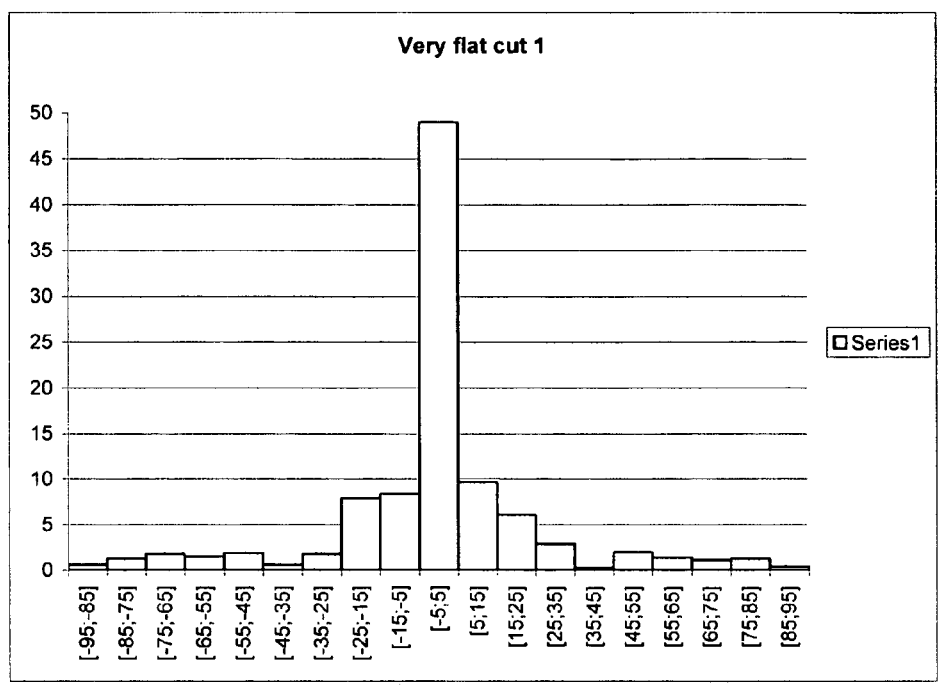

Referring to FIGS. 6d and 7d, it can be seen that, for a "flat stone" cut diamond, the majority of color streaks are positioned within a range of angles between plus and minus 35° from the plane of the observation position.

Therefore, this data shows that improved fire measurement readings can be obtained if the length of the boundary between the relatively reflective and relatively unreflective regions, at least, is greater than the minimum length in order to minimise the number of color streaks that jump completely from one region to another region in one rotational movement.

It will be appreciated that, with different shapes and/or symmetries of particular gemstone cut patterns, such as square, oval, pear, heart-shaped or irregular shapes, the algorithms used to determine the periphery of the gemstone and the various measurements of optical properties, as described above, may be varied to take into account the shape and symmetry of the particular gemstone cut pattern.

It will be appreciated that, with different shapes and/or symmetries of particular gemstone cut patterns, such as square, oval, pear, heart-shaped or irregular shapes, the configuration of relatively reflective regions 40 and relatively unreflective regions of concave surface 26, may be varied to take into account the shape and symmetry of the particular gemstone cut pattern. It will also be appreciated that the configuration of relatively reflective regions 40 and relatively unreflective regions of concave surface 26 may be varied to take into account a particular property being determined. For instance, when determining a measure of the fire of a gemstone, it is desirable to for relatively reflective regions 40 to be thin radial lines arranged around the axis 22, such that the light pattern reflected comprises relatively narrow peaks and relatively wide troughs. Thus, spectrally colored light will be generally less overpowered by white light and more visible.

It will be appreciated that in alternative embodiments, concave surface 26 may be held stationary within the apparatus and the platform is rotated instead. In this arrangement, the images captured of diamond 20 rotate and extra processing is required to take that into account when analysing those images. When comparing a first image at a first rotational position with a second image at a second different rotational position (and with subsequent third, fourth . . . images) processing must be performed so that pixels of the first and second (and subsequent) images correspond to the same region or regions of diamond 20. To achieve this, the second (and subsequent) image may be digitally rotated back about the point corresponding to the centre of rotation of the platform to correct for the rotation of diamond 20 in the images. Alternatively, when comparing selected pixels of a first and second (or subsequent) image, to obtain a measure of scintillation for example, the pixels of the second (or subsequent) image may be selected so as to correspond to a portion of the image rotated back about the point corresponding to the centre of rotation of the platform to correct for the rotation of diamond 20. However, due to limitations on the resolution of the captured images, accuracy of comparison is reduced in both cases and this arrangement is less preferable than the former arrangement in which the platform is stationary and concave surface 26 rotated.

It will be appreciated that in further alternative embodiments, concave surface 26 may be held stationary within the apparatus, and instead the camera 30 and the platform both rotated by a single or separate stepper motors in a coordinated fashion. This arrangement eliminates the need for extra processing to correct for the rotation of the images of diamond 20, but involves additional mechanical complexity and increased cost of manufacture.

While the above embodiments have described an apparatus arranged to i) support a gemstone having an axis of symmetry such that the axis of symmetry is parallel to the axis 22, ii) rotate the light pattern relative to the platform about the axis 22, and iii) capture images of the gemstone along the axis 22, it is important to realize that the present invention is not limited to this particular arrangement of the three axes. In particular, the axis of relative rotation between the light pattern and the platform need not be co-linear or even parallel to the axis 22 (ie from the axis parallel to an axis of symmetry of a gemstone when supported in the apparatus) and/or the axis along which the images are captured need not be co-linear or even parallel to the axis 22. Furthermore, the axis of relative rotation between the light pattern and the platform and the axis along which the images are captured need not be co-linear or even parallel between themselves.

According to some embodiments, a gemstone having an axis of symmetry may be supported in the apparatus such that the axis of symmetry, the axis of relative rotation between the light pattern and the means of support, and the axis along which the images are captured are coordinated such that i) the apparatus is able to take advantage of the shape and/or symmetry of the cut pattern of the particular gemstone when rotating the light pattern relative to the gemstone, and ii) the apparatus is able to capture images of the gemstone, such as images of the crown of a SRB cut diamond, from which features resulting from the shape and/or symmetry of the gemstone may be observed. For instance, the axis of relative rotation between the light pattern and the means of support may be at an angle of incidence to the axis of symmetry of up to about 30° without serious degradation to the performance of the apparatus. Similarly, the axis along which the images are captured may at an angle of incidence to the axis of symmetry of up to about 45° without serious degradation to the performance of the apparatus.

What is claimed is:

1. An apparatus configured to generate image data for use in determining a visual property of a gemstone, the apparatus comprising:
   a support structure configured to support the gemstone placed at an observation position, the support structure being configured to support the gemstone having an axis of symmetry such that the axis of symmetry is parallel to an X axis passing through the observation position;
   a light source configured to illuminate the gemstone with a spatially varied light pattern;
   a rotator, configured to rotate the gemstone relative to the light pattern substantially about the X axis;
   a camera arranged to capture electronic images of light of the gemstone and to output the images as image data; and
   a controller configured to control the rotator and the camera such that the camera is configured to capture an electronic image of the gemstone at each of a plurality of rotational positions of the support structure relative to the light pattern, the images being captured generally along the X axis;
   wherein the light source comprises a reflector having a concave surface arranged to reflect light generally towards the gemstone,
   wherein the concave surface has at least one relatively reflective region and at least one relatively unreflective region, whereby said light pattern is generated,
      wherein the length of a boundary between the relatively reflective and relatively unreflective regions is greater than the radial distance between the center and the edge of the concave surface.

2. An apparatus according to claim 1, wherein the boundary between the relatively reflective and relatively unreflective regions is curved.

3. An apparatus according to claim 2, wherein the boundary has a substantially spiral shape.

4. An apparatus according to claim 2, wherein the boundary comprises a plurality of boundary segments.

5. An apparatus according to claim 4, wherein the boundary segments are substantially straight.

6. An apparatus according to claim 4, wherein the boundary segments are curved.

7. An apparatus according to claim 4, wherein the boundary segments comprise straight segments and curved segments.

8. An apparatus according to claim 1, wherein, at each point along the boundary, an angle between the boundary and a line including the point and the center of the concave surface is in the range between about plus and minus 45 degrees.

9. An apparatus according to claim 1, wherein, at each point along the boundary, an angle between the boundary and a line including the point and the center of the concave surface is in the range between about plus and minus 35 degrees.

10. An apparatus according to claim 1, wherein, at each point along the boundary, an angle between the boundary and a line including the point and the center of the concave surface is in the range between about plus and minus 25 degrees from the plane of axis X.

11. An apparatus configured to generate image data for use in determining a property of a gemstone, the apparatus comprising:
- a support structure configured to support the gemstone at an observation position such that an axis of symmetry of the gemstone is substantially parallel to an axis of rotation of the apparatus;
- a light source, comprising a reflector having a concave surface arranged to reflect a spatially varied light pattern generally towards the observation position, the concave surface including at least one relatively reflective region and at least one relatively unreflective region and is configured to generate the light pattern, wherein the length of a boundary between the relatively reflective region and the relatively unreflective region is greater than the radial distance between the center and an edge of the concave surface; and
- a rotator configured to rotate the gemstone relative to the light pattern substantially about the axis of rotation.

12. An apparatus according to claim 11, wherein the boundary between the relatively reflective region and relatively unreflective region is curved.

13. An apparatus according to claim 12, wherein the boundary has a substantially spiral shape.

14. An apparatus according to claim 12, wherein the boundary comprises a plurality of boundary segments.

15. An apparatus according to claim 14, wherein the boundary segments are substantially straight.

16. An apparatus according to claim 14, wherein the boundary segments are curved.

17. An apparatus according to claim 14, wherein the boundary segments comprise straight segments and curved segments.

18. An apparatus according to claim 11, wherein, at each point along the boundary, an angle between the boundary and a line including the point and the center of the concave surface is in the range between about plus and minus 45 degrees.

19. An apparatus according to claim 11, wherein, at each point along the boundary, an angle between the boundary and a line including the point and the center of the concave surface is in the range between about plus and minus 35 degrees.

20. An apparatus according to claim 11, wherein, at each point along the boundary, an angle between the boundary and a line including the point and the center of the concave surface is in the range between about plus and minus 25 degrees from the plane of the X axis.

* * * * *